US005776462A

United States Patent [19]
Tsai et al.

[11] Patent Number: 5,776,462
[45] Date of Patent: Jul. 7, 1998

[54] POGOSTEMON CABLIN EXTRACT FOR INHIBITING H. INFLUENZAE ADHESION AND TREATING OTITIS MEDIA OR SORE THROAT

[75] Inventors: Hsiu-Hsien Tsai, Chang-Huah, Taiwan; Shie-Ming Hwang, Columbus, Ohio

[73] Assignee: Sage R&D, a partnership, Columbus, Ohio

[21] Appl. No.: 761,321

[22] Filed: Dec. 10, 1996

[51] Int. Cl.$^6$ .......................... A61K 35/78; A61K 47/00; A61K 9/68; A61K 9/20

[52] U.S. Cl. .................. 424/195.1; 424/439; 424/440; 424/441; 424/464; 514/888

[58] Field of Search ................... 424/195.1, 439, 424/440, 441, 464; 514/888

[56] References Cited

U.S. PATENT DOCUMENTS

| | | | |
|---|---|---|---|
| 4,784,853 | 11/1988 | Inoi et al. | 424/195.1 |
| 5,137,922 | 8/1992 | Shimamura et al. | 514/731 |

FOREIGN PATENT DOCUMENTS 3167132  7/1991  Japan.

OTHER PUBLICATIONS

Hong-Yen Hsu, Yuh-Pan Chen, Shun-Gi Hsu, Jau-Shin Hsu, Cheng-Jyh Chen, & Hsien-Chang Chang, Concise Pharmacognosy, New Medicine Publishing Co., Taipei, Taiwan, R.O.C., pp. 303–304 (1985).

Hsien-Chang Chang, Medicinal Herbs II, Holiday Publishing Co., Taipei, Taiwan, R.O.C., 67 (1991).

Woei-Song Kan, Pharmaceutical Botany, National Research Institute of Chinese Medicine, Taipei, Taiwan, R.O.C., 485 (1971).

Woei-Song Kan, Pharmaceutical Botany, National Research Institute of Chinese Medicine, Taipei, Taiwan, R.O.C., 475 (1971).

Morse et al., Haemophilus, Microbiology, Fourth Edition, published by J.B. Lipincott Company, pp. 615–618 (1990).

Stephens et al., Pathogenic Events During Infection of the Human Nasopharynx with Neisseria meningitis and Haemophilus influenza, Reviews of Infectious Diseases, 13:22–23 (1991).

Harada et al., Adherence of *Haemophilus influenzae* to nasal, nasopharyngeal and bucal epithelial cells from patients with otitis media, European Archives of Oto-rhino-laryngology, 247:122–124 (1990).

Stenfors et al., Abundant Attachment of Bacteria to Nasopharyngeal Epithelium in Otitis–Prone Children, The Journal of Infectious Diseases, 165:1148–1150 (1992).

Bakaletz et al., Frequency of Fimbriation on Nontypable *Haemophilus influenzae* and its Ability to Adhere to Chinchilla and Human Respiratory Epthelium, Infection and Immunity, 56: 331–335 (1988).

Weiser, Relationship between Colony Morphology and the Life Cycle of *Haemophilus influenzae*: the Contribution of Lipopolysaccharide Phase Variation to Pathogenesis, The Journal of Infectious Diseases, 168, 672–680 (1993).

Weiser, et al., Phase Variation in Pneumococcal Opacity: Relationship between Colonial Morphology and Nasopharyngeal Colonization, Infection and Immunity, 62, 2582–2589 (1994).

Nagai et al., Antiviral Research, 19:207–217, 1992.

Evans, Trease and Evans' Pharmacognosy, 13th Ed., Bailliere Tindall, London, GB, pp. 216–217, 1989.

Remington's Pharmaceutical Sciences, 18th Ed., Mack Publishing Co., Easton, PA, pp. 1519–1544, 1990.

The Merck manual of Diagnosis and Therapy, vol. 1, General Medicine, 15th Ed., Merck & Co., Inc., Rahway, NJ, pp. 131 and 132, 1987.

Ruoff, The Prokaryotes, 2nd Ed., vol. II, Springer-Verlag, New York, Inc., pp. 1450–1464, 1992.

Tortora et al., Microbiology, An Introduction, 5th Ed., The Benjamin/Cummings Publishing Co., Inc., pp. 390–393, 1995.

Ichikawa et al. Chem. Pharm. Bull. 37:345–348, 1989.

*Primary Examiner*—David M. Naff
*Assistant Examiner*—Janet M. Kerr
*Attorney, Agent, or Firm*—Donald O. Nickey; Standley & Gilcrest

[57] ABSTRACT

The attachment of *H. influenzae* to human cells such as oropharyngeal cells, is inhibited by aqueous extracts of the plants known as *Pogostemon cablin* and *Agastache rugosa*. The composition obtained from the aqueous extraction of the plants *Pogostemon cablin, Agastache rugosa* or mixtures thereof is also effective in preventing or treating Otitis media and sore throat. The plant extract may be contained in a liquid enteral product such as an infant formula or may be incorporated into lozenges, candies, chewing gums and the like. The plant extract may also be administered as a throat spray or nasally using drops or a spray. A process for the production of a medicinal product is also disclosed.

13 Claims, 4 Drawing Sheets

POGOSTEMON CABLIN EXTRACT FOR INHIBITING H. INFLUENZAE ADHESION AND TREATING OTITIS MEDIA OR SORE THROAT

FIELD OF THE INVENTION

This invention relates to the inhibition of *Haemophilus influenzae* (hereinafter "*H. Influenzae*") attachment to human cells, more specifically the nasopharynx system, and thereby provide for the prevention and treatment of *Otitis media* and sore throat in humans. In this invention an aqueous extract from the plant *Pogostemon cablin* or the plant *Agastache rugosa* is disclosed to treat and to effectively relieve humans from *H. Influenzae* infections, *Otitis media* and sore throat. The extracts of the plants have shown good anti-*H. Influenzae* activity in human trials and a neonatal rat model. *H. Influenzae* is a bacteria known to cause *Otitis media* and sore throat in humans.

BACKGROUND OF THE INVENTION

Modern medical science is constantly searching for new and more powerful agents to prevent, treat or retard bacterial and viral infections and cure the diseases they cause. Bacterial and viral infections of humans and domestic animals cost billions of dollars annually. Vast sums of money are spent each year by pharmaceutical companies to identify, characterize and produce new antibiotics and anti-virals to combat the emerging drug resistant strains which have become a serious problem. Reliable prophylactic treatments for disease prevention are also of major interest.

*Otitis media* is the second most common cause for outpatient visits by the pediatric population of the United States, following upper respiratory tract infections. Antibiotic and surgical approaches have been used for treatment. Non-typable *H. Influenzae* is associated with many cases of *Otitis media* and is considered the leading causative agent of chronic *Otitis media* with effusion.

A "sore throat" is common in humans. As used in this specification and the claims of this application, a "sore throat" means a condition characterized by pain or discomfort on swallowing. It may be due to any of a variety of inflammations of the tonsils, pharynx, or larynx. There are certain pathogens that are associated with sore throat in humans, they include Pneumococci, *H. Influenzae*, Streptococci and Staphylococci. Viruses such as *Coxsackie viruses*, *Herpes simplex virus*, *Influenza viruses* and *Parainfluenza viruses* are also known to be associated with sore throat. Antibiotic, anti-inflammatory, and soothing compositions (e.g. lozenges) have been used for the treatment of a sore throat.

The use of herbal drugs and folk medicines have been known for thousands of years in China. These herbal approaches to the treatment of numerous illnesses, from arthritis to viral infections, have been viewed by western modern medicine as ineffective and dangerous. Records of the use of herbs date from ancient China, Egypt and Biblical times. Early physicians used hundreds of herbs to treat a variety of ailments. The practice is still widespread, especially in Asia and Europe. During the 19th century, many home remedies containing herbs were patented and sold. Modern drugs have replaced those remedies, but many modern drugs contain ingredients derived from herbs.

In 1776, the English botanist and physician William Withering learned that an herbal tea made by an old farm woman was effective in treating dropsy, or excess water in the tissues, which is caused by the inability of the heart to pump strongly enough. He found that one ingredient of the tea, which was made with leaves of the foxglove plant, strengthened the heart's pumping ability. The drug made from the foxglove plant is now known as digitalis.

Folk medicine is a relatively modern term to the West and has come to mean the care and treatment of the sick through a variety of herbal medicines. In recent years, folk medicines have become of increasing interest to many people in the western scientific medical community.

PRIOR ART

An herbal medicine known as POGOSTEMI HERBA has been used to treat heatstroke, fever, headache, vomiting, chest and abdomen discomfort and intestinal disorders such as diarrhea. POGOSTEMI HERBA is known to be derived from the plants *Pogostemon cablin* and *Agastache rugosa*. As used in this specification and in the claims, the plants *Pogostemon cablin* and *Agastache rugosa* shall mean the plants identified in the book *Concise Pharmacognosy*, New Medicine Publishing Co., Taipei, Taiwan, R.O.C., at pages 303–304 (1985). The herbal medicine, POGOSTEMI HERBA, is known to be effective against common skin pathogens. See: Hong-Yen Hsu, Yuh-Pan Chen, Shun-Gi Hsu, Jau-Shin Hsu, Cheng-Jyh Chen, & Hsien-Chang Chang, *Concise Pharmacognosy*, New Medicine Publishing Co., Taipei, Taiwan, R.O.C., page 304 (1985). POGOSTEMI HERBA is prepared from either *Pogostemon cablin* or *Agastache rugosa*. Both plants belong to the Labiatae family.

*Pogostemon cablin* was originally produced in south Asia and south China. In Taiwan, it is cultivated as a commercial product. For more information on these plants, see Hsien-Chang Chang, *Medicinal Herbs II*, Holiday Publishing Co., Taipei, Taiwan, R.O.C., 67 (1991) and Woei-Song Kan, *Pharmaceutical Botany*, National Research Institute of Chinese Medicine, Taipei, Taiwan, R.O.C., 485 (1971). *Pogostemon cablin* (or patchouli) is a perennial plant which is cultivated in tropical Asia for a highly desired perfumary oil, patchouli oil. See H. Hikino, K. Ito and T. Takemoto, *Chem. Pharm. Bull.*, 16(8), 1608 (1968) and H. Itokawa, K. Suto and K. Takeya, *Chem. Pharm. Bull.*, 29(1), 254 (1981). *Agastache rugosa* is produced throughout China, Taiwan, Japan and Korea. See Woei-Song Kan, *Pharmaceutical Botany*, National Research Institute of Chinese Medicine, Taipei, Taiwan, R.O.C., 475 (1971).

*Pogostemon cablin* and *Agastache rugosa* are commercially utilized in China, Taiwan and Japan as a crude drug. Both plants have been consumed by humans for over 1,600 years. See: Hong-Yen Hsu, Yuh-Pan Chen, Shun-Gi Hsu, Jau-Shin Hsu, Cheng-Jyh Chen & Hsien-Chang Chang, *Concise Pharmacognosy*, New Medicine Publishing Co., Taipei, Taiwan, R.O.C., pp. 303–304 (1985); Woei-Song Kan, *Pharmaceutical Botany*, National Research Institute of Chinese Medicine, Taipei, Taiwan, R.O.C., 485 (1971) and Woei-Song Kan, *Pharmaceutical Botany*, National Research Institute of Chinese Medicine, Taipei, Taiwan, R.O.C., 475 (1971).

Extracts of *Pogostemon cablin* have been used for treating heatstroke, vomiting, diarrhea, fever, headache, chest and abdomen discomfort and pain. See Hong-Yen Hsu, Yuh-Pan Chen, Shun-Gi Hsu, Jau-Shin Hsu, Cheng-Jyh Chen & Hsien-Chang Chang, *Concise Pharmacognosy*, New Medicine Publishing Co., Taipei, Taiwan, R.O.C., pp. 303–304 (1985); and Hsien-Chang Chang, *Medicinal Herbs II*, Holiday Publishing Co., Taipei, Taiwan, R.O.C., 67 (1991); and Woei-Song Kan, *Pharmaceutical Botany*, National Research Institute of Chinese Medicine, Taipei, Taiwan, R.O.C., 485 (1971).

*Agastache rugosa* is used as a flavoring agent and has been used for treating chest discomfort, vomiting, diarrhea, and abdomen pain caused by indigestion. See Woei-Song Kan, *Pharmaceutical Botany*, National Research Institute of Chinese Medicine, Taipei, Taiwan, R.O.C., 475 (1971).

Pharmacologically, the herbal medicine POGOSTEMI HERBA has been known as an agent effective against gastrointestinal maladies (anti-emetic and anti-diarrhea effect), to promote secretion of gastric juice and enhance digestion (stomachic effect), expand blood capillaries (antipyretic effect), and treat common skin pathogens (antifungal effect). A valuable component of these plants are the extractable oils and the volatile oils. These oils are commonly used in the perfume and flavoring industries.

To date the prior art has not suggested nor disclosed the use of aqueous extracts of the *Pogostemon cablin* (*P. cablin*) or *Agastache rugosa* (*A. rugosa*) plants to inhibit the attachment of *H. Influenzae* to human cells, which results in the prevention and treatment of disease states such as *Otitis media* and sore throat. More generally, the present invention is also applicable to the treatment of *Otitis media* and sore throat caused by other pathogens.

Haemophilus are small, gram-negative, non-motile, non-spore forming bacilli with complex growth requirements. Diseases caused by *H. influenzae* usually begin as a nasopharyngitis, possibly precipitated by a viral infection of the upper respiratory tract. See Morse et al., *Haemophilus*, Microbiology, Fourth Edition, published by J. B. Lipincott Company, pages 615–618 (1990).

*H. influenzae* are spread from person to person by airborne respiratory droplets or direct contact with secretions. To colonize, *H. influenzae* must contend with ciliary clearance mechanisms of the nasopharyngeal mucosal surface and the mucous barrier. Once past the mucous barrier and the ciliary escalator, *H influenzae* attach to mucosal epithelial cells. Invasion of mucosal surfaces appears to be an important characteristic of pathogenic bacteria. See Stephens et al., *Pathogenic Events During Infection of the Human Nasopharynx with Neisseria meningitis and Haemophilus influenza*, Reviews of Infectious Diseases, 13:22–23 (1991). It has further been reported that *H. influenzae* harbored in the nasopharynx are a key factor in the development of middle ear infections (Otitis media), and that non-typable *H. influenzae* adhere to nasopharyngeal and nasal mucosal cells. See Harada et al., *Adherence of Haemophilus influenzae to nasal, nasopharyngeal and bucal epithelial cells from patients with otilis media*, European Archives of Oto-rhino-laryngology, 247:122–124 (1990). Stenfors et al., *Abundant Attachment of Bacteria to Nasopharyngeal Epithelium in Otitis-Prone Children*, The Journal of Infectious Diseases, 165:1148–1150 (1992). In accordance with the present invention an aqueous extract of the plants *P. cablin* or *A. rugosa* are employed to inhibit the adhesion of *H. influenzae* to human cells which will provide efficacy in the treatment of *Otitis media* and sore throat.

SUMMARY OF THE INVENTION

There is disclosed a method of inhibiting the attachment of *H. influenzae* to human cells by administering to a human, a therapeutically effective amount of a composition comprising an aqueous extract of at least one plant selected from the groups consisting of *Pogostemon cablin* and *Agastache rugosa*.

There is also disclosed a method of treating or preventing *Otitis media* and sore throat in a human, said method comprising administering to said human an effective amount of a composition comprising at least one aqueous extract from at least one plant selected from the group consisting of *Pogostemon cablin* and *Agastache rugosa*. More generally, the present invention is directed to the prevention and treatment of *Otitis media* and sore throat through the administration of the plant extracts described herein.

The present invention also relates to a process to isolate the efficacious compounds from the recited plants and to the isolated compounds themselves.

The plant extracts, once isolated from the plant material, may be concentrated and then placed in compositions for the administration to a human. The compositions may take a variety of forms such as throat and nasal sprays, candies, lozenges, gels, tablets, beverages, nutritional products and the like. What is important to the effective use of these plant extracts is that the extract come into contact with the epithelial cells of the nose and throat.

Dosages of at least 0.4 gms per day of the extracts characterized in FIGS. 1 and 3 have been found to be effective. Dosages as high as 20 gms per day do not result in serious side effects.

There is further disclosed a method of inhibiting the attachment of *H. influenzae* to human oropharyngeal cells by administering via a nasal passageway a formulation containing a therapeutically effective amount of at least one material obtained from the aqueous extraction of at least one plant selected from the group consisting of *Pogostemon cablin* and *Agastache rugosa*.

The present invention also relates to a method of inhibiting the attachment of *H. influenzae* to human oropharyngeal cells by administering a throat spray formulation containing a therapeutically effective amount of the plant extract.

In the method according to this invention the human may be an adult, child or infant. Infants, children and the elderly will benefit greatly from the present invention as this group of humans is particularly susceptible to *H. influenzae* infections. One aspect of this invention is the need for the plant extracts to contact the mouth and throat areas so as to prevent, inhibit or disturb the attachment of *H influenzal* to human oropharyngeal cells. Thus, for infants, an infant formula containing the hereinafter described plant extracts will be effective in treating or preventing the attachment of *H. influenzae* cells to the oropharyngeal cells of the infant and thus prevent or treat *Otitis media* and/or sore throat caused by *H. infuenzae*. For children and adults, a medical food or nutritional product, such as milks and yogurts, containing the plant extracts described herein will also be effective in treating or preventing *Otitis media* and sore throat in humans caused by *H. influenzae* and/or other pathogens.

Also disclosed is a medicinal product produced by the process comprising the steps of a) contacting comminuted plant material selected from the group consisting of *Pogostemon cablin*, *Agastache rugosa*, and mixtures thereof, with water to form an aqueous plant material; b) heating the aqueous plant material to about 100° C. and holding at that temperature for about 0.5 to about 3 hours; c) separating the insoluble plant material from the aqueous phase; and d) concentrating the solute contained in the aqueous phase. The concentrated solute may then be subjected to freeze drying, spray drying, evaporation or ultrafiltration.

There is further disclosed a medicinal product wherein the product is characterized by a C18-HPLC profile as set forth in FIG. 1 a nd an HPSEC profile as set forth in FIG. 3.

In a preferred embodiment, the plant extracts are incorporated into tablets, lozenges, chewing gums or jellies that dissolve in the mouth and bathe the nasopharynx of the patient. These and other aspects of the invention will become apparent to those skilled in the art as a result of the following examples which are intended as illustrative of the invention and not limitative.

BRIEF DESCRIPTION OF THE DRAWINGS

To acquaint persons skilled in the art with the principles of the invention, reference is made to the attached drawings which form a part of this specification.

FIG. 1 is an HPLC UV profile at 214 nm of extract P10E-1 (FIG. 1A) and Extract P10E-2 (FIG. 1B) wherein the injection volume was 60 μL;

FIG. 2 is an HPLC UV profile at 214 nm of extract P10E-1 spiked with acetaminophen (FIG. 2A) and extract P10E-2 spiked with acetaminophen (FIG. 2B) wherein the injection volume was 60 μL;

FIG. 3 is an HPSEC UV profile at 214 nm of P10E-1 (FIG. 3A) and an HPSEC UV profile at 214 nm of P10E-2 (FIG. 3B) wherein the injection volume was 100 μL; and FIG. 4 is an HPSEC UV profile at 214 nm of P10E-1 spiked with acetaminophen (FIG. 4A) and an HPSEC UV profile at 214 nm of P10E-2 spiked with acetaminophen (FIG. 4B) wherein the injection volume was 100 μL.

Figure 1A:
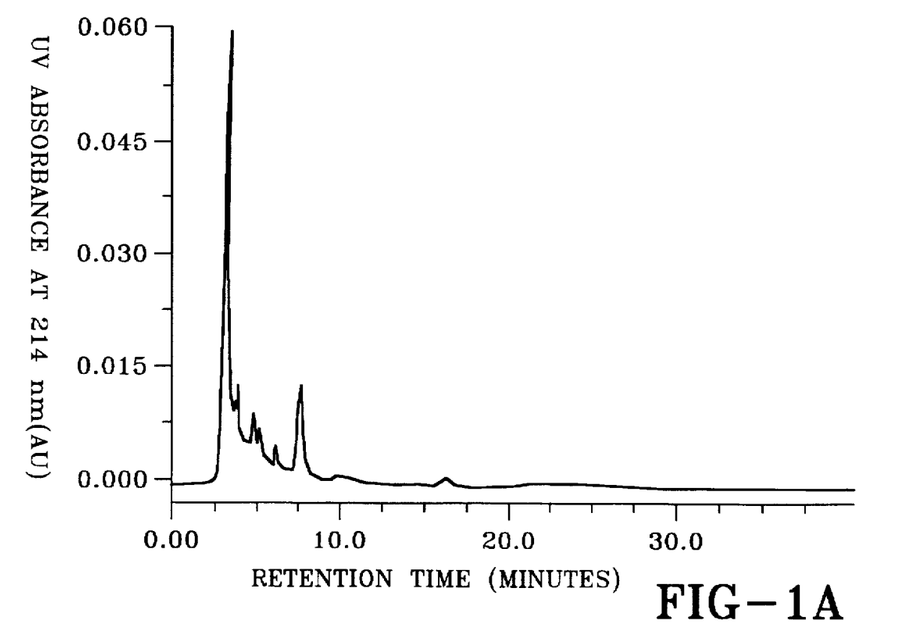
Figure 1B:
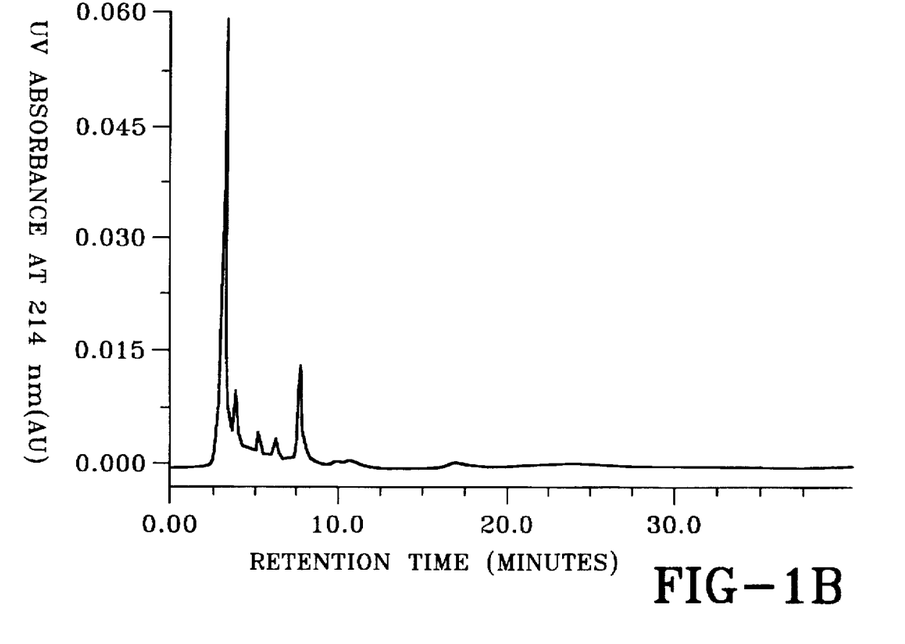
Figure 3A:
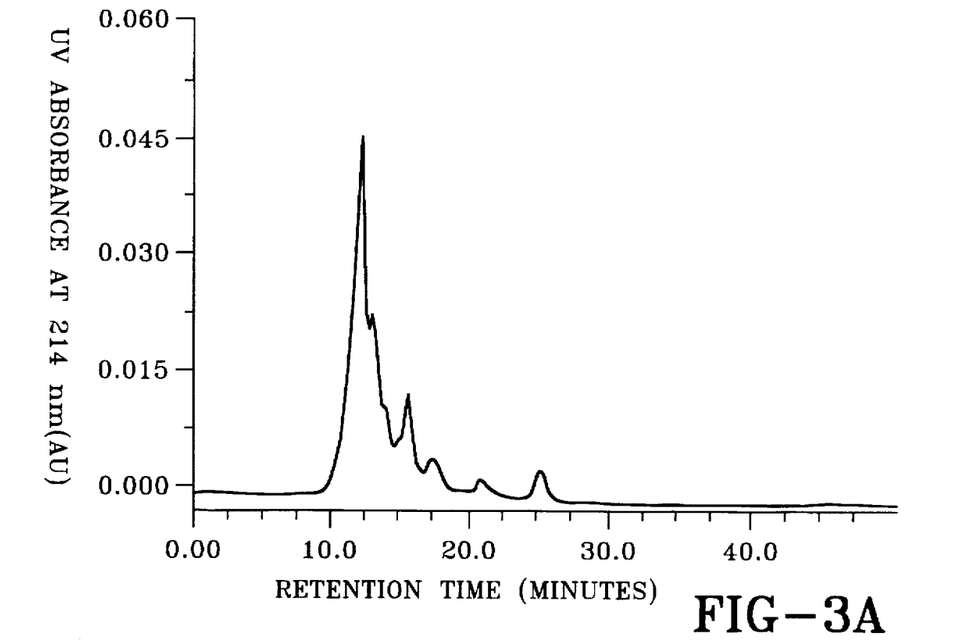
Figure 3B:
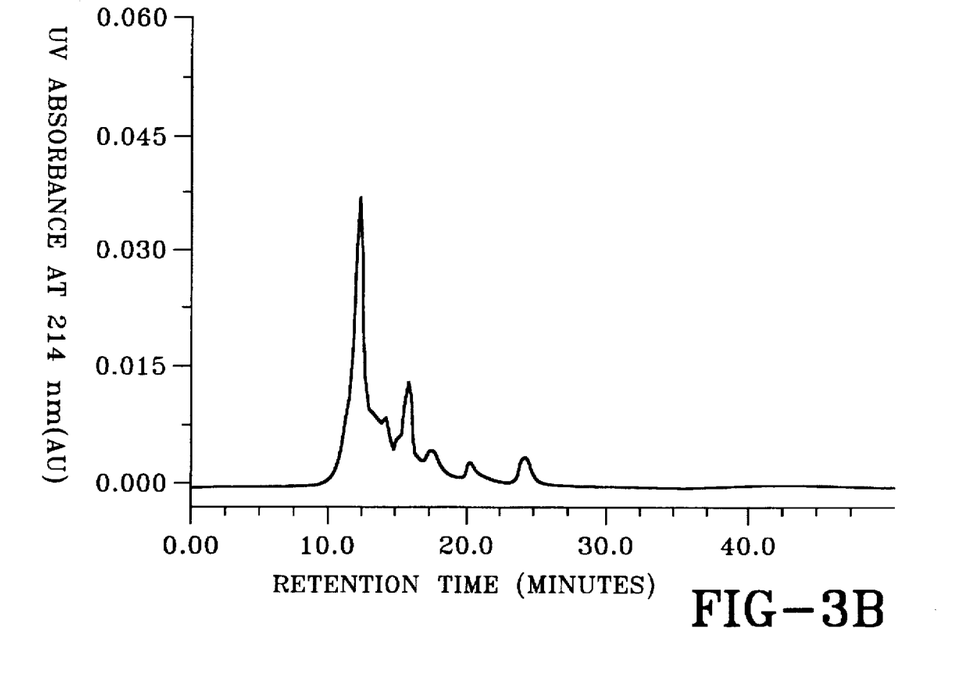

One aspect of the present invention is directed to the compositions of matter which comprise the plant extracts as characterized by the HPLC profiles of FIGS. 1A and 1B and the HPSEC profiles of FIGS. 3A and 3B.

BEST MODE FOR CARRYING OUT THE INVENTION

To acquaint persons skilled in the art with the principles of the invention, the following Examples are submitted which are intended to be illustrative and not limitative.

EXAMPLE I

Preparation of Extracts

A. In this method of extraction, plants, including stem, leaves and roots, of *Pogostemon cablin* and *Agaslache rugosa* were obtained, washed with cold water, dried and comminuted. The plant materials were then extracted twice with boiling water on a basis of 1 part by weight of plant material to approximately 5 to 10 parts by weight of water. The amount of water used should at least cover the plant material in the extraction vessel. Samples were boiled for one hour, but not in excess of 3 hours, in order to allow effective extraction of the desired components. Volatile oils and other volatile components were removed during the extraction. The aqueous solution may be separated from the plant material by filtration and then freeze dried, spray dried or reduced in volume by heating with or without an applied vacuum.

B. Using the traditional method of preparing herbal extracts for medicinal use or a health food, a portion (e.g., about 10% by weight) of the plant material was ground to a powder and used to absorb the aqueous extract prepared in A. above.

C. Another traditional method uses starch to absorb the extract from A. above and thus prepare the herbal medicine.

The prepared herbal medicine is then used "as is" or placed into a paper or cloth bag, or formulated into a lozenge, candy, throat spray or nasal spray. Those skilled in the art will appreciate how such means of administration can be prepared.

In a preferred embodiment, an appropriate amount of the herbal medicine is placed in a paper or cloth bag (such as a tea bag) and then placed in an aqueous media at a temperature up to 100° C. The bag is removed from the media and the liquid is orally consumed. In another embodiment the powdered herbal medicine is placed into warm or cold water and consumed orally.

Dosages range from 1 to 5 treatments per day at about 0.4 to 20 grams per dosage depending upon the form and concentration of the herbal medicine. The effective minimum dose of a composition as characterized in FIGS. 1 and 3, is 0.4 gms per day. Dosages as high as 20 grams per day can be accomplished without serious side effects.

EXAMPLE II

Clinical Evaluation

The extract powder prepared in Example IB of *Pogostemon cablin* (HHT888-10) was administered orally to a patient (male, age 48) with recurrent *Otitis media* at a dosage of 2 g twice a day ( total 4 gms per day) for 3 days. The symptoms associated with *otitis media* promptly subsided. In another episode, the same patient had a sore throat and was treated with HHT888-10 at a dosage of 2 g b.i.d. p.o. for 1 day. The sore throat also promptly subsided. Two additional patients (female, ages 45 and 18) with sore throats were also treated with HHT888-10 at the same dosage for 1 day and their sore throats subsided. A fourth patient (male, age 40) with a sore throat took HHT888-10 at the same dosage for 1.5 days (total dose 6 g) and his sore throat completely subsided. This fourth patient had a history of sulfa drug allergy which prevented conventional drug therapies.

A fifth patient (male, age 15) was treated due to sore throat and otalgia with HHT888-10 at 2 g b.i.d. p.o. The symptoms subsided after administration of one unit dose ( i.e., 2 g). A sixth patient (male, age 44) was treated for sore throat, headache and fever. Initial treatment with Erythromycin, Bactrium, and Naproxen subsided the fever and headache. However, the sore throat became worse. On the fifth day, the patient was treated with HHT888-10 at 2 g b.i.d. p.o. for 2 days. The sore throat then subsided. On the twelfth day after the first sore throat subsided the sore throat reappeared. Upon treatment with HHT888-10 at 2 g b.i.d. for 2 days, the sore throat subsided. A seventh patient (female, age 43) had a sore throat and was treated with HHT888-10 at 2 g b.i.d. for 2 days. Her sore throat subsided after three unit doses (i.e., 6 g).

Clinical evaluation of the herbal medicine according to this invention has shown that foods fried in animal or vegetable oils should be avoided during administration.

EXAMPLE III

*H. Influenzae* Testing

Two 2.0 g samples of HHT888-10 prepared as described in Example 1 were extracted twice respectively with 20 mL of water and aqueous $NH_4HCO_3$ (0.1 N) each time. Each sample was extracted by vortexing with the solvent for 1 minute and standing for 1 hour with occasional shaking and vortexing.

The extract was separated from the insoluble material by centrifuge at 2000 rpm for 40 minutes. Each supernate was filtered through a 0.22-μm filter. Each extract was then reduced in volume by nitrogen flow, and then freeze dried for weighing. The freeze-dried weight and % recovery of each extract are listed in Table I along with the pH of the first extract. P10E-1 was the extract using aqueous 0.1 N. NH$_4$HCO$_3$ as the extracting solvent. P10E-2 was the extract prepared by using water as the sole extracting solvent.

TABLE I

| Extract | Extracting Solvent | pH of 1st Extract | FD'd Weight | % Recovery* |
|---|---|---|---|---|
| P10E-1 | 0.1 N, NH$_4$HCO$_3$ | 7.72 @ 24.5° C. | 403.5 mg | 20.1% |
| P10E-2 | Water | 5.58 @ 24.7° C. | 370.7 mg | 18.5 |

*of the original HHT888-10

Each of the above freeze-dried extracts, P10E-1 and P10E-2 of HHT888-10, were tested for anti-*H. influenzae* activity in a neonatal rat model.

Haemophilus influenzae

*Haemophilus influenzae* (*H. influenzae*) cultures (fimbriated, nontypable) which have been implicated in *Otitis media* were obtained from Dr. Lauren Bakeletz of The Ohio State University, Columbus, Ohio, U.S.A. The use of these organisms in assays has been described in Bakaletz et al., *Frequency of Fimbriation of Nontypable Haemophilus influenzae and its Ability to Adhere to Chinchilla and Human Respiratory Epthelium*, Infection and Immunity, 56: 331–335 (1988). The *H. influenzae* were streaked onto Chocolate agar plates (BBL-Becton Dickinson & Co., Cockeysville, Md., U.S.A.) from frozen aliquots of a low passage number and incubated at 37° C. in a 5% CO$_2$ incubator for about 18 hours to obtain logrithmically growing cultures. The *H. influenzae* was used in neonatal rat model assay as described below.

The neonatal rat model was used to demonstrate the in vivo activity of the herbal medicine according to this invention in inhibiting the attachment of *H. influenzae* to nasopharynx cells. The attachment of the *H. influenzae* to the mammal's nasopharynx area is the first step of a bacterial infection which later may develop into *Otitis media* and other diseases. More specifically, a neonatal rat model was used to test the in vivo activity of the herbal medicine according to this invention against nontypable *Haemophilus influenzae*. The test was modified from an infant rat model described in: 1) "Journal of Infectious Diseases", 168, 672–680 (1993); and 2) "Infection and Immunity", 62, 2582–2589 (1994). In these experiments, 24-hour-old or younger rat pups were used in place of the prescribed 5-day-old rats in the publications. This model is the best known model for the study of the nasopharyngeal colonization and pathogenesis of *H influenzae*. To test the in vivo activity of the herbal medicines according to this invention against *H. influenzae*, overnight cultures of *H. influenzae* were prepared as described above, washed twice and diluted with Hank's Balanced Saline Solution (HBSS) to obtain a bacterial suspension of less than 100,000 colony forming units (CFU) per mL. Sample solutions of P10E-1 and P10E-2 were prepared by dissolving in HBSS at 4 and 2 mg/mL. The sample solution was mixed with an equal volume (1 ml) of the diluted bacterial suspension and incubated for 1 hour at 37° C. A control of 1 ml HBSS was also mixed and incubated with an equal volume of the diluted bacterial suspension.

The Experimental and Control mixtures were used to inoculate rat pups at 10 μl per animal intranasally. 24 hours after administration, samples of nasopharyngeal fluid were obtained by the slow instillation of 25 μL of HBSS into the left naris and the initial 10 μL discharge from the right naris was collected for obtaining a plate count. This procedure ensured that the fluid had passed through the nasopharynx. The nasal wash was then spread "as is" or diluted and then spread onto chocolate agar plates. The plates were incubated at 37° C. overnight and counted for the number of CFU's (an indicator of the number of viable bacteria). Table II sets forth the results of this experiment.

TABLE II

In Vivo Activity of P10E-1 and P10E-2 Against *H. Influenzae*

| Treatment* | Trial** | Inoculum Dose CFU/pup*** | *H.I.* Recovered Log$_{10}$ (CFU/mL) |
|---|---|---|---|
| HI + HBSS (untreated) | 1 | 630 | 2.82 ± 0.73 |
| HI + HBSS 3X (untreated) | 1 | 630 | 3.17 ± 0.88 |
| HI + P10E-1 @ 2 mg/mL | 1 | 480 | 0.00 ± 0.00**** |
| HBSS (uninfected) | 1 | 0 | 1.36 ± 0.69 |
| HI + HBSS (untreated) | 2 | 720 | 3.13 ± 0.75 |
| HI + P10E-1 @ 2 mg/mL | 2 | 780 | 2.17 ± 0.95 |
| HBSS (uninfected) | 2 | 0 | 1.24 ± 0.58 |
| HI + HBSS (untreated) | 3 | 190 | 4.75 ± 0.11 |
| HI + P10E-1 @ 1 mg/mL | 3 | 440 | 2.04 ± 0.69 |
| HI + P10E-2 @ 1 mg/mL | 3 | 210 | 2.54 ± 0.67 |
| HBSS (uninfected) | 3 | 0 | 2.53 ± 0.75 |

*HI = nontypable *H influenzae*
HBSS = Hanks' balanced saline solution
HBSS 3X = additional HBSS were added intranasally twice at 10 μL each, one at 2 hours and one at 8 hours post inoculation. This was done to determine if the two additional washes would affect the level of bacteria recovered.
** = ten pups per group
*** = Individually determined for each inoculum.
**** = 0.00 value is indicative of no bacteria found in the lavage fluid.

As Table II shows, three trials were conducted. The first (trial 1) was at an inoculum dose of 480 CFU/animal. The second (trial 2) was at a higher inoculum dose, 780 CFU/animal and the third (trial 3) was at a slightly lower inoculum dose, 210–440 CFU/animal. All showed reduction (1 to 3 logs in CFU/mL) in the recovered bacteria when compared with the untreated group. Each group consisted of 10 rat pups (age≦24 hours). In trial 1, no bacteria was found in the lavage fluid of all ten rat pups infected with inoculum preincubated with 2 mg/mL of P10E-1 for 1 hour at 37° C. In trial 3, the recovered bacteria of both groups treated with 1 mg/mL of P10E-1 and P10E-2, respectively, were at or below those of the uninfected group, i.e., the background level. Thus, these results demonstrate that the compositions according to this invention are active inhibitors of the proliferation of *H. influenzae* in the nasopharynx of neonatal rats.

These data demonstrate the in vivo activity of aqueous extracts of *Pogostemon cablin* and *Agastache rugosa* in inhibiting the attachment of *H. influenzae* to nasopharynx cells and one skilled in this art would logically predict, in conjunction with the previously recited clinical data, that administration of the inventive herbal medicine or its active extracts or components would be efficacious in preventing *Otitis media* caused by nontypable *H. influenzae* in a human being.

EXAMPLE IV

In this experiment, the anti-*H. influenzae* aqueous ammonium bicarbonate and water extracts, P10E-1 and P10E-2, of HHT888-10 as described in Example III were tested for solubility and characterized by reversed-phase high performance liquid chromatography (RP-HPLC), high performance size exclusion chromatography (HPSEC), and ultrafiltration.

Both P10E1 and P10E-2 were light brown powders. Both powders were soluble in water, aqueous ammonium bicarbonate solution (pH 7.8–8.1), and Hanks' balanced saline solution (pH 6.5). P10E1 and P10E2 were also soluble in aqueous ammonium bicarbonate solutions containing 20% alcohol (90.5% ethanol - 4.5% methanol - 5.0% isopropanol) by volume. Both extracts became progressively less soluble in aqueous ammonium bicarbonate solutions containing 30% and more alcohol by volume. Both P10E-1 and P10E-2 were not or only barely soluble in a 0.2N aqueous ammonium bicarbonate solution containing 85% of alcohol by volume.

Both P10E-1 and P10E-2 are stable to air, as evidenced by their efficacy in the neonatal rat assay against *H. influenzae* 44 days after being prepared and stored in glass vials under a nominal atmosphere (see Example III). The active component or components of P10E-1 and P10E-2 were also stable to heat, as their predecessor HHT888-10 was heated in boiling water for one hour or longer during extraction from the plant material as described in Example I.

Figure 2A:
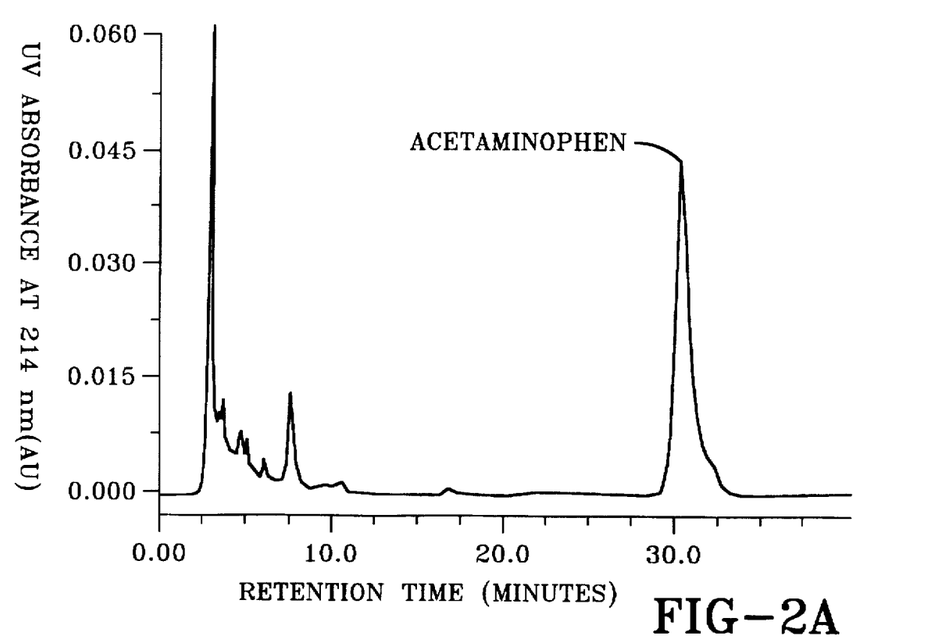
Figure 2B:
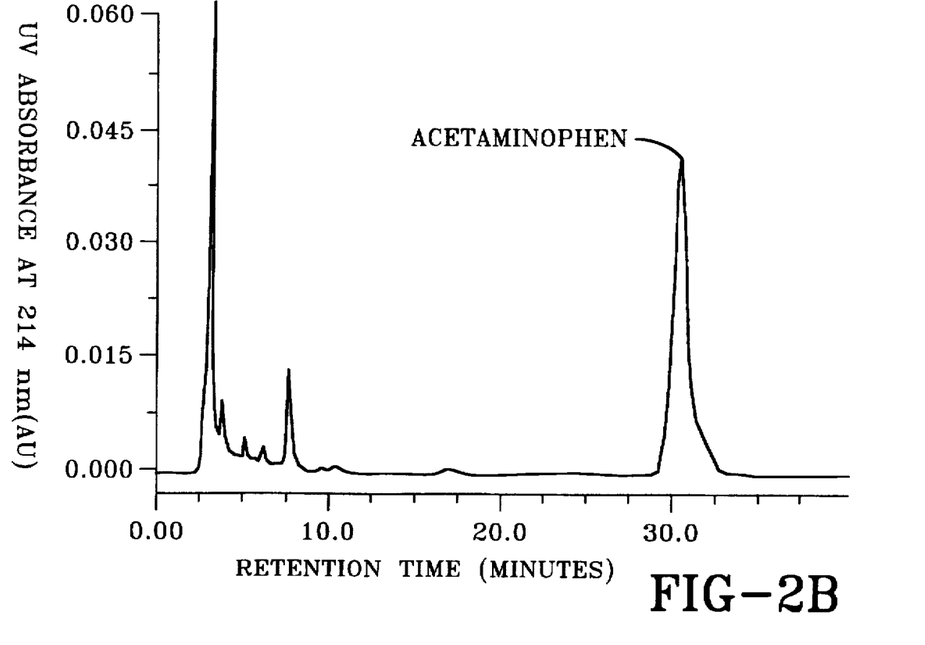

A Rainin Microsorb-MV™ C18 column (5-μm particle size, 100-Å pore size, 4.6 mm ID×25 cm L) was used for the RP-HPLC analysis. As set forth in FIGS. 1 and 2, C18-HPLC means an RP-HPLC that uses a silica column that has been modified with covalently bonded hydrocarbon molecules of eighteen carbon atoms. A Varian MicroPake® TSKgel G3000PWXL column (7.8 mm ID×30 cm L) with a TSK PWXL guard column (6.0 mm ID×4.0 cm L) was used for the HPSEC analysis. The same HPLC system, comprising a Waters 600E pump, a Waters 712 WISP auto sample injector, a Beckman 160 UV/VIS absorbance detector, an Anspec ANS-3114 in-line vacuum degasser, and a Waters 825 Maxima chromatography workstation was used for both C18-HPLC and HPSEC analyses.

For the C18-HPLC analysis, the mobile phase was EtOH/ 0.2N NH$_4$HCO$_3$ (2/98, v/v), where EtOH stands for a reagent alcohol consisting of 90.5% ethanol, 4.5% methanol, and 5.0% isopropanol. The flow rate was 0.80 mL/min. Samples of P10E-1 and P10E-2 were prepared in the mobile phase at 1.0 mg/mL and each was filtered through a 0.45-μm syringe filter before injection. The injection volumes were 30 and 60 μL and the run time was 40 minutes. The UV detection was at 214 nm and 0.030 AUFS. Spiked samples of P10E-1 and P10E-2 containing 0.01 mg/mL of acetaminophen (USP reference standard, lot H-1) as an internal reference standard were also prepared from the same 1.0 mg/mL solutions and analyzed.

For the HPSEC analysis, the mobile phase was EtOH/ 0.2N NH$_4$HCO$_3$ (20/80, v/v) at a flow rate of 0.80 mL/min. Samples were prepared in the mobile phase at 1.0 mg/mL. The injection volume was 100 μL and the run time was 50 minutes. The UV detection was at 214 nm and 0.030 AUFS. Spiked samples containing 0.01 mg/mL of acetaminophen were also prepared from the same 1.0 mg/mL P10E-1 and P10E-2 solutions and analyzed for comparison.

Figure 4A:
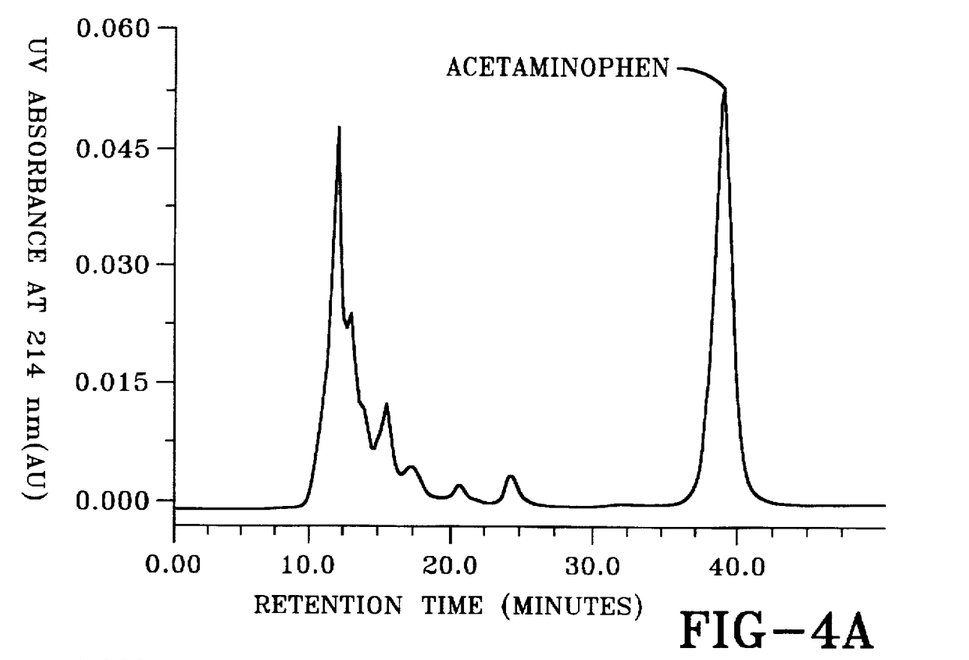
Figure 4B:
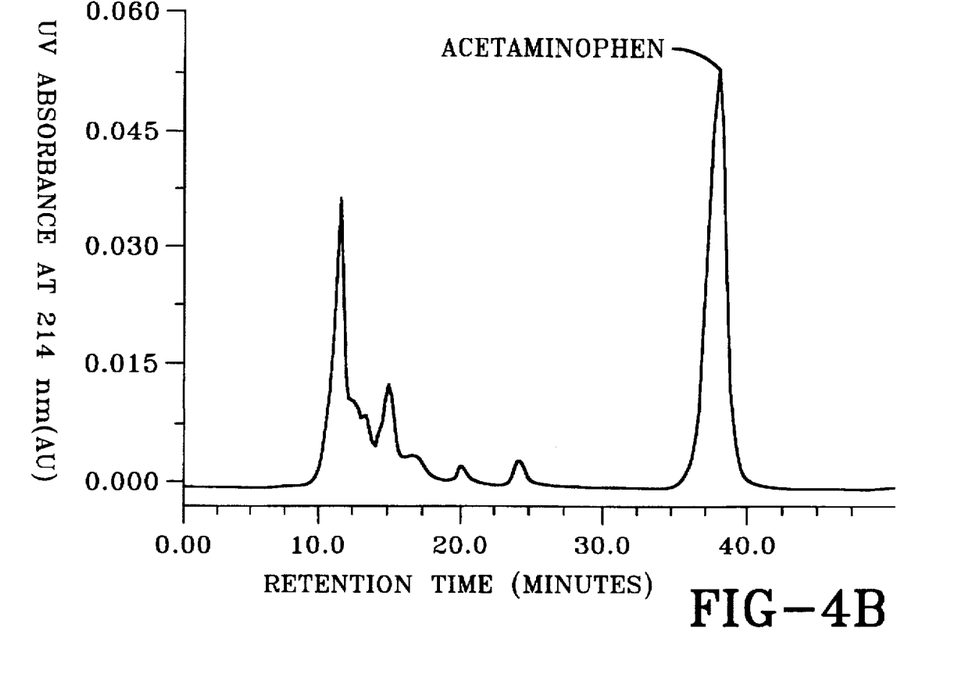

FIG. 1 shows the C18-HPLC profiles of P10E-1 and P10E-2 at 60 μL injection. FIG. 2 shows the C18-HPLC profiles of the same P10E-1 and P10E-2 spiked with acetaminophen as an internal reference standard. FIG. 3 shows the HPSEC profiles of P10E-1 and P10E-2 at 100, μL injection. FIG. 4 shows the HPSEC profiles of the same P10E-1 and P10E-2 samples spiked with acetaminophen. The UV response of each C18-HPLC peak was linearly proportional to the injection volume, such as at 30 and 60 μL. Both the C18-HPLC and HPSEC profiles were reproducible. Acetaminophen or N-acetyl-p-aminophenol is the active principle of Tylenol® for pain and fever relief. It is a phenol derivative with an acetylamino group on the benzene ring at the para position to the hydroxyl group.

The results of this experiment demonstrate that P10E-1 and P10E-2 each contains a number of components. Fifteen peaks are detectable in the C18-HPLC profile of P10E-1, and are labeled as such in FIG. 1A. Fifteen peaks are also detectable for P10E-2 as shown in FIG. 1B. The C18-HPLC peaks of P10E-1 and P10E-2 are essentially the same, except peak 2 is missing for P10E-2 and peak 6 is much smaller for P10E-2. An additional small peak between peaks 7 and 8 is also found in P10E-2.

Twelve peaks are detectable in the HPSEC profile of P10E-2, as shown in FIG. 3B. The same HPSEC peaks are also detectable in the HPSEC profile of P10E-1 as shown in FIG. 3A, except peak 2 is missing in P10E-1. It is noted that the resolution of HPSEC is lower than that of C18-HPLC. More than one component can be expected to coelute in one HPSEC peak, such as peaks 3, 4, 5 and 8.

Table III summarizes the typical elution time of each of the C18-HPLC and HPSEC peaks of P10E-1, P10E-2 and acetaminophen as shown in FIGS. 1 through 4. The elution time of each peak in either C18-HPLC or HPSEC was determined from four injections, except that of acetaminophen which was determined from at least 2 injections. It should be noted that the C18-HPLC peaks mayormay not correlate with the HPSEC peaks. The peak elution time may shift under different HPLC or HPSEC systems and conditions.

TABLE III

C18-HPLC and HPSEC Elution Times of P10E-1, P10E-2 and Acetaminophen Peaks

| C18-HPLC | | HPSEC | |
| --- | --- | --- | --- |
| Peak No. | Elution Time (min) | Peak No. | Elution Time (min) |
| 1 | 3.0 | 1 | 7.1–7.2 |
| 2 | 3.5 | 2 | 9.0 |
| 3 | 3.7–3.8 | 3 | 11.4 |
| 4 | 4.0 | 4 | 12.4–12.5 |
| 5 | 4.3 | 5 | 13.3–13.5 |
| 6 | 4.7 | 6 | 14.3–14.6 |
| 7 | 5.0–5.1 | 7 | 14.9–15.1 |
| 8 | 6.0–6.1 | 8 | 16.5–16.9 |
| 9 | 6.8–7.0 | 9 | 20.0–20.5 |
| 10 | 7.4–7.6 | 10 | 21.0–21.5 |
| 11 | 9.5–9.6 | 11 | 24.1–24.8 |
| 12 | 10.0–10.5 | 12 | 41.3–44.2 |
| 13 | 6.1–16.8 | Acetaminophen | 37.7–38.4 |
| 14 | 17.1–17.3 | | |
| 15 | 21.3–22.7 | | |
| Acetaminophen | 30.0 | | |

The results of C18-HPLC an alysis show that all detectable components of P10E-1 and P10E-2 are more polar and less lipophilic than acetaminophen. All detectable peaks of P10E-1 and P10E-2 were eluted before that of acetaminophen, as shown in FIG. 2. The last detectable peak (peak 15 of P10E-1 and P10E-2) was a small and broad peak with a typical elution time of 21 to 23 minutes. The typical elution time of the acetaminophen peak was 30 minutes. The main peaks, 1 and 10, are clearly polar and UV absorbing materials. Peak 10 is slightly less polar than peak 1.

The results of this experiment, primarily from the HPSEC analysis, indicate that both P10E-1 and P10E-2 contain fairly small molecules. Almost all peaks were eluted at 11.4 minutes and later. From previously conducted experiments using sucrose and a polysaccharide standard, it was known that sucrose (MW 342.3 dalton) eluted at around 12.1 minutes while the elution time of the polysaccharide standard of MW 5,800 dalton was at around 9.9 minutes.

The small molecule characteristics of P10E-1 and P10E-2 was further confirmed with an ultrafiltration experiment. Two (2) milliliters of each of the above 1.0 mg/mL P10E-1 and P10E-2 solutions in EtOH/0.2N NH$_4$HCO$_3$ (20/80, v/v) spiked with 0.01 mg/mL acetaminophen was filtered in sequence through two Filtron Microsep™ ultrafiltration membranes, one with an MW cutoff at 3,000 dalton and one at 1,000 dalton. The retentate on the 3,000 dalton membrane was washed twice with 2.0 mL of EtOH/0.2N NH$_4$HCO$_3$ (20/80, v/v) each time. The retentate on the 1,000 dalton membrane was washed once with the second filtrate from the 3,000 dalton membrane. The ultrafiltration separations were conducted by centrifuge at 5,000×g for six hours at 25° C., using an IEC Centra-MP4R centrifuge and a 45° fixed angle rotor (No. 809).

The washed retentate on the 3,000 dalton membrane was dissolved in 2.0 mL of EtOH/0.2N NH$_4$HCO$_3$ (20/80, v/v) as the fraction with molecular weights (MW) greater than 3,000 dalton. The retentate on the 1,000 dalton membrane was dissolved in the third filtrate from the 3,000 dalton membrane as the fraction with MW between 1,000 and 3,000 dalton. The two filtrates from the 1,000 dalton membrane were the fractions with molecular weights of less than 1,000 dalton. All three fractions of each acetaminophen spiked P10E-1 and P10E-2 samples were analyzed by HPSEC under the same conditions as described above. Their HPSEC profiles were compared with those before the ultrafiltration separation.

The results showed that all peaks passed through the 1,000 dalton membrane, except peaks I and 2 which were retained on the 3,000 dalton membrane. That means, almost all components of P10E-1 and P10E-2 are small molecules with molecular weights of less than approximately 1,000 dalton. Only a very small amount of molecules (peaks 1 and 2) in P10E-1 and P10E-2 are larger than 3,000 dalton.

In the HPSEC analysis, acetaminophen (MW 151.2) was eluted at 38 minutes when EtOH/0.2N NH$_4$HCO$_3$ (20/80, v/v) was the mobile phase at a flow rate of 0.80 mL/min (FIGS. 3 and 4). This was much longer than the elution time of 19.4 minutes as expected for an HPSEC column with a total bed volume of 15.5 mL. The delay of the peak elution was caused by a lipophilic interaction between acetaminophen and the column packing. Thus, when the alcohol content of the mobile phase increased progressively from 20% to 85% in volume, the elution time of acetaminophen decreased correspondingly from 38 minutes to 16 minutes, as expected. Similarly, the peaks 6–12 of P10E-1 and P10E-2 moved towards shorter elution time as the alcohol content of the mobile phase increased.

The main peak 3 of P10E-1 and P10E-2, on the contrary, shifted towards slightly longer elution time as the alcohol content of the mobile phase increased. This shift may be partially due to the loss of the material on the column as it becomes less soluble in the mobile phase with more alcohol content.

Industrial Applicability

It can be concluded from the foregoing experiments that aqueous extract from the plants known as *Pogostemon cablin* and *Agastache rugosa* will inhibit the attachment of *H. influenzae* to human cells. Furthermore, inasmuch as *H influenzae* have been identified in the literature as being associated with *Otitis media* and sore throat, it can be concluded that the above identified herbal extracts may be employed in the prevention and treatment of *Otitis media* and sore throat in humans.

The therapeutic effects described in the preceding paragraph may be provided by an enteral liquid nutritional product, such as infant formula, containing one or more of the herbal extracts. It can be further concluded that the attachment of *H. influenzae* to human oropharyngeal cells may be inhibited by administering via a nasal passageway, or as a throat spray, a formulation containing a therapeutically effective amount of at least one of the extracts characterized in FIGS. 1 and 3.

Products containing the extracts of this invention are effective in inhibiting the attachment or disturbing the attachment of *H. influenzae* to human cells thereby treating or preventing maladies such as *Otitis media* and sore throat which are associated with *H influenzae* infections. The effectiveness of the extracts of the invention are also present following digestion and absorption of the extract as demonstrated by the clinical outcome of the patient with recurrent *Otitis media* described in Example II.

The medical community is constantly in search of methods and products that will prevent or lessen the severity of *H. influenzae* infections. The extracts and products containing the extracts according to this invention will be readily accepted by the medical community as an additional tool in the prevention and treatment of this common problem.

While preferred embodiments of the invention have been disclosed, it will be apparent to those skilled in the art that various changes and modifications may be made therein without deviating from the spirit or scope of this invention.

What is claimed is:

1. A method of inhibiting the attachment of *H influenzae* to human cells by orally or nasally administering to a human, a therapeutically effective amount of a composition comprising an aqueous extract of *Pogostemon cablin* wherein said extract has an HPLC profile selected from FIG. 2A or 2B or an HPSEC profile selected from FIG. 4A or 4B under conditions wherein peaks in the HPLC or HPSEC profile are eluted relative to the acetaminophen peak.

2. The method of claim 1 wherein the human is a child or an infant.

3. The method of claim 1 wherein the therapeutically effective amount of said extract is at least 0.4 gms per day.

4. The method of claim 1 wherein said composition containing said -extract is in a form selected from the group consisting of pills, tablets, jellies, lozenges, powders, candies, confections, gels, nutritional supplements, chewing gums, medical nutritionals, infant nutritionals, beverages, yogurts, milk and aqueous solutions.

5. A method for the treatment or prevention of *Otitis media* in a human, said method comprising orally or nasally administering to said human an effective amount of a composition comprising an aqueous extract of *Pogostemon cablin* wherein said extract has an HPLC profile selected from FIG. 2A or 2B or an HPSEC profile selected from FIG. 4A or 4B under conditions wherein peaks in the HPLC or HPSEC profile are eluted relative to the acetaminophen peak.

6. The method of claim 5 wherein the human may be a child or an infant.

7. The method of claim 5 wherein the therapeutically effective amount of said extract is at least 0.4 gms per day.

8. The method of claim 5 wherein said human is an infant and said composition is an infant formula.

9. The method of claim 5 wherein said composition containing said extract is in the form of a tablet, lozenge, jelly or a chewing gum that dissolves in the mouth to bathe the nasopharynx of said human.

10. A method for the treatment or prevention of sore throats in a human, said method comprising orally or nasally administering to said human an effective amount of a composition comprising an aqueous extract of *Pogostemon cablin* wherein said extract has an HPLC profile selected from FIG. 2A or 2B or an HPSEC profile selected from FIG. 4A or 4B under conditions wherein peaks in the HPLC or HPSEC profile are eluted relative to the acetaminophen peak.

11. The method of claim 10 wherein said composition containing said extract is in a form selected from the group consisting of pills, tablets, jellies, lozenges, powders candies, confections, gels, nutritional supplements, chewing gums, medical nutritionals, infant nutritionals, beverages, yogurts, milk and aqueous solutions.

12. The method of claim 10 wherein the therapeutically effective amount of said extract is at least 0.4 gms per day.

13. The method of claim 10 wherein said composition containing plant extract is in the form of a tablet, lozenge, jelly or a chewing gum that dissolves in the mouth to bathe the nasopharnyx of said human.

* * * * *